(12) United States Patent
Terada (10) Patent No.: US 8,003,085 B2
(45) Date of Patent: Aug. 23, 2011

(54) WATER-BASED SHAMPOO

(75) Inventor: Eiji Terada, Tokyo (JP)

(73) Assignee: Kao Corporation, Tokyo (JP)

( * ) Notice: Subject to any disclaimer, the term of this patent is extended or adjusted under 35 U.S.C. 154(b) by 581 days.

(21) Appl. No.: 11/500,341

(22) Filed: Aug. 8, 2006

(65) Prior Publication Data

US 2007/0031365 A1    Feb. 8, 2007

(30) Foreign Application Priority Data

Aug. 8, 2005 (JP) ................................. 2005-230182

(51) Int. Cl.
*A61K 8/89* (2006.01)
*A61K 8/72* (2006.01)
(52) U.S. Cl. .................................. 424/70.12; 424/70.11
(58) Field of Classification Search ................ 424/70.12
See application file for complete search history.

(56) References Cited

U.S. PATENT DOCUMENTS 5,085,857 A    2/1992 Reid et al.
2005/0255074 A1*   11/2005 Hanada et al. ........... 424/70.122

FOREIGN PATENT DOCUMENTS

| EP | 1 283 030 A1 | | 2/2003 |
|---|---|---|---|
| JP | 2004-526806 | * | 9/2004 |
| WO | WO 99/44567 | | 9/1999 |

OTHER PUBLICATIONS

Wing Li et al. Maximizing Shampoo Performance. Jul. 2006 http://www.personalcaremagazine.com/Story.aspx?Story=1216.*
Polydimethylsiloxane viscosities from GE Silicones (see attached polydimethylsiloxane document).*
Chinese Office Action mailed Aug. 27, 2010 in corresponding Chinese Application No. 200610110692 (submitting English Translation only).

* cited by examiner

*Primary Examiner* — Shanon A Foley
*Assistant Examiner* — Sarah Alawadi
(74) *Attorney, Agent, or Firm* — Oblon, Spivak, McClelland, Maier & Neustadt, L.L.P.

(57) ABSTRACT

There is provided a shampoo capable of exhibiting a smooth feel of hair upon shampooing and rinsing and imparting good luster and manageability to finished hair. The water-based shampoo of the present invention contains silicone oil droplets dispersed therein wherein said oil droplets is composed of at least (A) 50 to 90% by mass of polydimethylsiloxane and (B) 2 to 50% by mass of a copolymer having a block chain constituted of an amino-modified organopolysiloxane chain and a polyoxyalkylene chain.

7 Claims, 2 Drawing Sheets

WATER-BASED SHAMPOO

FIELD OF THE INVENTION

The present invention relates to water-based shampoos in which oil droplets made of a specific kind of silicone blend are dispersed, and which exhibit a smooth feel upon shampooing and rinsing and impart good luster, manageability and smoothness to finished hair.

BACKGROUND OF THE INVENTION

In conventional shampoos, water-insoluble silicones have been widely used for the purpose of imparting a good conditioning effect to hair. However, the shampoos containing such water-insoluble silicones are still unsatisfactory in adhesion of the water-insoluble silicones to hair damaged by chemical treatments with hair coloring agents or permanent treatment agents, and there tends to arise such a problem that hair treated therewith suffers from entangling and frictional feel upon shampooing or rinsing as well as dry and rough feel after drying.

To solve the above problems, JP 10-45544A discloses a shampoo composition for hair care which is individually blended with a water-insoluble silicone having a viscosity of 100 Pa·s or less and at least one aminated silicone (hereinafter referred to as an "amino-modified silicone"). However, when the water-insoluble silicone and the amino-modified silicone are individually blended in the shampoo composition, it has been confirmed that adhesion of the water-insoluble silicone to hair is not improved, and hair treated with the shampoo composition still suffers from dry and rough feel after drying. Further, the amino-modified silicone described in JP 10-45544A contains an alkylene amine bonded to a polysiloxane side chain thereof and, therefore, exhibits a high hydrophobicity, thereby causing such a problem that frictional feel of hair upon foaming and rinsing is increased.

On the other hand, JP 2004-526806A discloses a hair treatment composition containing oil droplets obtained from a blended mixture of a water-insoluble silicone having a viscosity of at least 100,000 mm²/s as measured at 25° C. and an amino-modified silicone. The hair treatment composition is improved in adhesion of the water-insoluble silicone to hair. However, since the hair treatment composition contains the amino-modified silicone similarly to the composition of JP 10-45544A, there also arises such a problem that hair treated therewith suffers from frictional feel upon foaming and rinsing and, therefore, tends to be still insufficient in smoothness after drying.

SUMMARY OF THE INVENTION

The present invention relates to a water-based shampoo capable of exhibiting a smooth feel of hair upon shampooing and rinsing and imparting good luster, manageability and smoothness to finished hair.

As a result of intense and extensive studies, it has been found that the shampoo containing oil droplets obtained by blending a polydimethylsiloxane with a copolymer having a block chain constituted of an amino-modified organopolysiloxane chain and a polyoxyalkylene chain can satisfies the above requirements.

According to the present invention, there is thus provided a water-based shampoo comprising silicone oil droplets dispersed therein, said oil droplets comprising at least (A) 50 to 90% by mass of polydimethylsiloxane and (B) 2 to 50% by mass of a copolymer having a block chain constituted of an amino-modified organopolysiloxane chain and a polyoxyalkylene chain.

The shampoo of the present invention exhibits a smooth feel of hair upon shampooing and rinsing and imparts good luster, manageability and smoothness to finished hair.

EXPLANATION OF REFERENCE NUMERALS

1: Hair; 10: Container; 20: Lid; 21: First protrusion; 22: Second protrusion; 23: Foam guiding wall; 24: Pin for inhibiting entrainment of hair; 25: Filling inlet; 30: Motor; 50: Metering device; 51: Water filling inlet; 60: Torque detector

DETAILED DESCRIPTION OF THE INVENTION

The polydimethylsiloxane as the component (A) includes those compounds represented by the following general formula (2):

wherein R is a methyl group or a hydroxyl group; and m is a number of 1 to 20,000.

The polydimethylsiloxane as the component (A) preferably has a viscosity of 100,000 mm²/s or less, more preferably 50,000 mm²/s or less and still more preferably 20,000 mm²/s or less as measured at 25° C. in view of good smoothness upon foaming and rinsing as well as less stickiness after drying. Examples of commercially available products of the polydimethylsiloxane include KF-96A-5cs, KF-96A-10cs, KF-96A-100cs, KF-96A-1000cs, KF-96A-5000cs, KF-96H-10000cs, KF-96H-50000cs, KF-96H-100000cs and KF-96H-1000000cs all available from Shin-Etsu Silicone Co., Ltd. These polydimethylsiloxanes may be used alone or in combination of any two or more thereof. As the polydimethylsiloxane, there may also be used commercially available products put on the market in the form of a mixture of the polydimethylsiloxane with a liquid cyclic silicone such as octamethylcyclotetrasiloxane, decamethylcyclopentasiloxane and tetradecamethylcyclohexasiloxane.

The content of the polydimethylsiloxane as the component (A) in the silicone oil droplets is in the range of 50 to 98% by mass, preferably 70 to 97% by mass and still more preferably 85 to 95% by mass in view of good smoothness upon foaming and rinsing as well as less stickiness after drying.

The component (B) contained in the silicone oil droplets is a copolymer having a block chain constituted of an amino-modified organopolysiloxane chain and a polyoxyalkylene chain which copolymer is represented by the following general formula (1):

wherein $R^1$ is a hydrogen atom or a monovalent hydrocarbon group having 1 to 6 carbon atoms; $R^2$ is $R^1$ or E; E is a group represented by $-R^3-Z$ wherein $R^3$ is a direct bond or a divalent hydrocarbon group having 1 to 20 carbon atoms, and Z is a primary, secondary or tertiary amino-containing group or an ammonium-containing group; Y is a divalent group; a is a number of 2 or more; b is a number of 1 or more; n is a number of 2 to 10; c is a number of 4 or more; d is a number of 2 or more; and a plurality of the $R^1$ groups, a plurality of the $R^2$ groups and a plurality of the E groups are respectively the same or different.

In the general formula (1), a plurality of the $R^1$ groups are preferably each independently a hydrogen atom, an alkyl group having 1 to 6 carbon atoms or a phenyl group, more preferably methyl or ethyl, and still more preferably methyl.

$R^3$ is preferably a linear or branched alkylene chain having 1 to 6 carbon atoms such as methylene, ethylene, trimethylene, propylene and tetramethylene groups, and more preferably a trimethylene or propylene group.

Z is preferably an amino-containing group or an ammonium-containing group which are respectively represented by the following general formulae (3) and (4):

wherein $R^4$ is

-continued
$-OCH_2CH_2-$, $-OCHCH_2-$,
            $\phantom{xxx}$|
            $\phantom{xxx}$$CH_3$ $-OCH_2CHCH_2-$, $-OCH_2CH-$
$\phantom{xxxxx}$|$\phantom{xxxxxxxxxx}$|
$\phantom{xxxxx}$OH$\phantom{xxxxxxxx}$$CH_2OH$ $R^5$ and $R^6$ are respectively a hydrogen atom or a monovalent hydrocarbon group having 1 to 3 carbon atoms, and $R^5$ and $R^6$ may be the same or different; e and f are respectively an integer of 0 to 6; and $T^-$ is a halogen ion or an organic anion.

Examples of the preferred E group in the general formula (1) include $-(CH_2)_3-NH_2$, $-(CH_2)_3-N(CH_3)_2$, $-(CH_2)_3-NH-(CH_2)_2-NH_2$, $-(CH_2)_2-NH-(CH_2)_2-N(CH_3)_2$ and $-(CH_2)_3-N^+-(CH_3)_3Cl^-$. Among these groups, more preferred is $-(CH_2)_3-NH-(CH_2)_2-NH_2$. Specific examples of $T^-$ include halogen ions such as chlorine ion, iodine ion and bromine ion, and organic anions such as methosulfate, ethosulfate, methophosphate and ethophosphate.

Examples of the preferred organic divalent group represented by Y in the general formula (1) include alkylene groups and arylene groups. Among these groups, more preferred are ethylene, propylene, trimethylene, n-butylene and i-butylene groups, and most preferred are n-butylene and i-butylene groups.

In the general formula (1), a is preferably a number of 2 to 1000, b is preferably a number of 1 to 50, c is preferably a number of 4 to 200, and d is preferably a number of 2 to 100.

In the block copolymer represented by the general formula (1), the content of the siloxane block is preferably 25 to 97% by mass, more preferably 35 to 90% by mass and still more preferably 50 to 80% by mass on the basis of a whole amount of the copolymer. The block copolymer preferably has an average molecular weight of at least 1200. Meanwhile, the average molecular weight used herein is such a value measured by an ordinary GPC method using chloroform as an eluant and polystyrene as a standard substance.

The "siloxane block" used herein means a siloxane containing two $R^1$ groups which is represented by the formula: $-[Si(R^1)_2-O]-$. Also, the "content of the siloxane block" means a ratio of a molecular weight of the siloxane block to a molecular weight of the block copolymer (1) which is expressed by mass %. When the content of the siloxane block lies within the above-specified range, the adhesion of the block copolymer (1) to hair can be enhanced, and the resultant shampoo can impart a smooth feel to hair upon foaming and rinsing.

Examples of the more preferred block copolymer include amino-modified polysiloxane-polyoxyalkylene block copolymers having a polymer block represented by the general formula (5):

wherein a, b and d have the same meanings as defined above; g is a number of 4 or more; and h is a number of 0 to 30.

In the general formula (5), a is preferably a number of 2 to 1000; b is preferably a number of 1 to 50; g is preferably a number of 4 to 200; and d is preferably a number of 2 to 100. The moiety of the polymer unit represented by $-O(C_2H_4O)_g(C_3H_6O)_h-$ may be in the form of either a block copolymer or a random copolymer. The component (B) used in the present invention may be produced, for example, by the method described in JP 9-183854A. Examples of commercially available products of the component (B) include "FZ-3789" and "SILICONE SS-3588" both available from Toray Dow Corning Silicone Co., Ltd.

The kinematic viscosity of the component (B) used in the present invention is preferably 10 mm$^2$/s or more, more preferably 100 mm$^2$/s or more, still more preferably 1000 mm$^2$/s or more and most preferably 5000 mm$^2$/s or more, and preferably 1000000 mm$^2$/s or less and more preferably 100000 mm$^2$/s or less. When the kinematic viscosity of the component (B) lies within the above-specified range, the amount of the residual component (B) adhering onto hair is suitably increased, and the resultant shampoo can impart a smooth feel to hair upon foaming and rinsing.

Meanwhile, the viscosity may be measured at 25° C. using a B-type viscometer while operating a rotor No. 2 at 6 rpm.

The amino equivalent of the component (B) used in the present invention is preferably 300 g/mol or more and more preferably 600 g/mol or more, and preferably 10000 g/mol or less, more preferably 5000 g/mol or less and still more preferably 2500 g/mol or less. When the amino equivalent of the component (B) lies within the above-specified range, the amount of the residual component (B) adhering onto hair is suitably increased, and the resultant shampoo can impart a smooth feel to hair upon foaming and rinsing.

Meanwhile, the amino equivalent (g/mol) may be measured by subjecting an ethanol solution of the block copolymer to titration using hydrochloric acid having a known concentration.

These components (B) may be used alone or in combination of any two or more thereof. The content of the copolymer having a block chain constituted of an amino-modified organopolysiloxane chain and a polyoxyalkylene chain as the component (B) in the oil droplets made of the silicone blend is in the range of 2 to 50% by mass, preferably 3 to 30% by mass and more preferably 5 to 15% by mass in view of good smoothness upon foaming and rinsing as well as less stickiness after drying.

The silicone blend composed of the components (A) and (B) may be in the form of a simple mixture of silicones, and is preferably in the form of a mechanically prepared water-based emulsion. Upon preparing such a water-based emulsion, at least one kind of emulsifier is preferably added thereto in order to stabilize the resultant emulsion.

Examples of the emulsifier include nonionic activators such as polyoxyethylene alkyl ethers, polyoxyethylene alkylphenyl ethers, polyoxyethylene sorbitan fatty esters, polyoxyethylene glyceryl fatty esters, polyoxyethylene hardened castor oils, polyethylene glycol fatty esters, polyglycerin fatty esters, sucrose fatty esters and polyether-modified silicones; cationic activators such as alkyltrimethylammonium chlorides, dialkyldimethylammonium chlorides, alkyldimethylamine salts, alkoxydimethylamine salts and alkylamidodimethylamine salts; anionic activators such as sodium dodecylbenzenesulfonate, sodium alkylsulfates, ammonium alkylsulfates, sodium polyoxyethylenealkylether sulfates, ammonium polyoxyethylenealkylether sulfates, coconut oil fatty acid potassium salts, coconut oil fatty acid methyl taurine sodium salts.

The water-based emulsion of the silicone blend of the present invention may be produced, for example, by the method of mixing the silicone component (A), the silicone component (B) and the emulsifier with each other; while slowly adding water to the resultant mixture under stirring, mixing the mixture at a high speed using a high-shear mixer upon phase conversion from W/O emulsion to O/W emulsion; and then while adding a remaining amount of water to the resultant emulsion, mixing the emulsion again at a high speed using a high-shear mixer.

The particle size of the water-based emulsion may be optionally changed by varying kind and amount of the emulsifier used as well as an agitation rotating speed of the high-shear mixer.

The particle size of the silicone emulsion is preferably 100 μm or less, more preferably 50 μm or less, still more preferably 10 μm or less and further still more preferably 4 μm or less in view of good stability of the silicone emulsion. Also, the average particle size of the silicone emulsion is preferably 0.1 μm or more from the standpoint of good feel upon use and good conditioning effect. Meanwhile, the particle size of the silicone emulsion has the same meaning as a particle size of the oil droplets made of the silicone blend in the water-based shampoo. Therefore, the particle size of the oil droplets made of the silicone blend is preferably within the above-specified range.

The particle size of the silicone emulsion may be measured by a particle size measuring apparatus using a laser scattering, for example, "LS-130" available from Coulter Inc.

The oil droplets may be composed of either a single kind of silicone blend or two or more kinds of silicone blends. More specifically, different kinds of silicone blends which are previously prepared separately may be used in combination with each other. The content of the oil droplets made of the silicone blend in the shampoo composition of the present invention is preferably 0.01 to 10% by mass, and more preferably 0.1 to 5% by mass and still more preferably 0.5 to 2% by mass in view of good smoothness upon from shampooing to rinsing as well as less stickiness after drying.

The water-based shampoo of the present invention may also contain an anionic surfactant in order to attain a high washability and a good foaming property. Examples of the anionic surfactant include sulfuric acid-based surfactants, sulfonic acid-based surfactants and carboxylic acid-based surfactants. Specific examples of the anionic surfactant include alkylsulfates, polyoxyalkylenealkylether sulfates, polyoxyalkylenealkenylether sulfates, salts of sulfosuccinic alkyl esters, sulfosuccinic alkylenealkylphenylether sulfates, alkanesulfonic acid salts, higher fatty acid salts, and alkylethercarboxylic acids or salts thereof. Among these anionic surfactants, preferred are polyoxyalkylenealkylether sulfates and alkylsulfates, and more preferred are those compounds represented by the following general formula (6) or (7):

R'O(CH$_2$CH$_2$O)$_n$SO$_3$M     (6), or

R'OSO$_3$M     (7)

wherein R' is an alkyl or alkenyl group having 10 to 18 carbon atoms; M is an alkali metal, an alkali earth metal or an ammonium group; and n is a number of 1 to 5 on the weight average.

Among them, in view of attaining both rapid foaming and good feel upon foaming, especially preferred are polyoxyethylenealkylether sulfates represented by the above general formula (6) in which R' is an alkyl group having 12 to 14 carbon atoms; n is 1 on the weight average; and M is ammonium or sodium.

These anionic surfactants may be used alone or in combination of any two or more thereof. The content of the anionic surfactant in the shampoo composition of the present invention is preferably from 1 to 30% by mass, more preferably from 5 to 25% by mass and still more preferably from 8 to 20% by mass in view of good foaming, liquid properties upon use and good washability.

The water-based shampoo of the present invention may further contain a nonionic surfactant or an amphoteric surfactant to improve washing performance thereof.

Examples of the nonionic surfactant include polyoxyalkylene sorbitan fatty esters, polyoxyalkylene sorbitol fatty esters, polyoxyalkylene glycerol fatty esters, polyoxyalkylene fatty esters, polyoxyalkylene alkyl ethers, polyoxyalkylene alkyl phenyl ethers, polyoxyalkylene (hardened) castor oils, sucrose fatty esters, polyglycerol alkyl ethers, polyglycerol fatty esters, fatty acid alkanol amides, alkyl glycosides, monoalkyl glyceryl ethers and monoalkenyl glyceryl ethers. Among these nonionic surfactants, preferred are alkyl glycosides, polyoxyalkylene (C$_8$ to C$_{20}$) fatty esters, polyoxyethylene sorbitan fatty esters, polyoxyethylene hardened castor oils, fatty acid alkanol amides, monoalkyl glyceryl ethers and monoalkenyl glyceryl ethers.

The fatty acid alkanol amides may be in the form of either a monoalkanol amide or a dialkanol amide, and are preferably those containing an acyl group having 8 to 18 carbon atoms and preferably 10 to 16 carbon atoms. The fatty acid alkanol amides, are more preferably those containing a hydroxyalkyl group having 2 to 3 carbon atoms. Specific examples of the fatty acid alkanol amides include oleic acid diethanol amide, palm kernel oil fatty acid diethanol amide, coconut oil fatty acid diethanol amide, lauric acid diethanol amide, polyoxyethylene coconut oil fatty acid monoethanol amide, coconut oil fatty acid monoethanol amide, lauric acid isopropanol amide and lauric acid monoethanol amide.

The alkyl or alkenyl group in the monoalkyl glyceryl ethers or the monoalkenyl glyceryl ethers is preferably a linear or branched alkyl group having 4 to 10 carbon atoms and preferably 8 to 10 carbon atoms. Specific examples of the alkyl group include n-butyl, isobutyl, n-pentyl, 2-methylbutyl, isopentyl, n-hexyl, isohexyl, n-heptyl, n-octyl, 2-ethylhexyl, n-decyl and isodecyl. Among these alkyl groups, preferred are 2-ethylhexyl and isodecyl.

Examples of the amphoteric surfactant include betaine-based surfactants. Among these betaine-based surfactants, preferred are alkyldimethylaminoacetic acid betaines, fatty amide propyl betaines and alkylhydroxysulfobetaines, and more preferred are fatty amide propyl betaines. The fatty amide propyl betaines are preferably those containing an acyl group having 8 to 18 carbon atoms and more preferably 10 to 16 carbon atoms. Among these fatty amide propyl betaines, especially preferred are lauramide propyl betaine, palm kernel oil fatty amide propyl betaine and coconut oil fatty amide propyl betaine.

These nonionic surfactants and amphoteric surfactants may be respectively used alone or in combination of any two or more thereof in the water-based shampoo of the present invention. In the case where the water-based shampoo of the present invention is used in the form of an aqueous shampoo solution, the fatty amide propyl betaines, the fatty acid alkanol amides or the monoalkyl glyceryl ethers are more preferably used therein because of not only good foamability but also adequate liquid properties of the obtained shampoo solution.

The content of the nonionic surfactant or the amphoteric surfactant in the water-based shampoo of the present invention is preferably from 0.1 to 15% by mass, more preferably from 0.5 to 8% by mass and still more preferably from 1 to 6% by mass in view of good foaming effect.

The water-based shampoo of the present invention may also contain a water-soluble cationic polymer in order to enhance a conditioning effect.

Specific examples of the water-soluble cationic polymer include cationized cellulose derivatives, cationic starches, cationized guar gum derivatives, diallyl quaternary ammonium salt/acrylamide copolymers, vinylimidazolium trichloride/vinylpyrrolidone copolymers, hydroxyethyl cellulose/dimethyldiallylammonium chloride copolymers, vinylpyrrolidone/quaternarized dimethylaminoethyl methacrylate copolymers, polyvinylpyrrolidone/alkylaminoacrylate copolymers, polyvinylpyrrolidone/alkylaminoacrylate/vinyl caprolactam copolymers, vinylpyrrolidone/methacrylamidopropyltrimethylammonium chloride copolymers, alkyl acrylamide/acrylate/alkylaminoalkylacrylamide/polyethylene glycol methacrylate copolymers, adipic acid/dimethylaminohydroxypropylethylenetriamine copolymers (e.g., "Caltaretin" available from Sandos Inc.; US), and cationic polymers described in JP 53-139734A and JP 60-36407A. Among these water-soluble cationic polymers, preferred are cationized cellulose derivatives, cationized guar gum derivatives and diallyl quaternary ammonium salt/acrylamide copolymers.

Further, as the water-soluble cationic polymer, there may also be used commercially available products such as, for example, "MERQUAT 550" (available from NALCO Co.; copolymer of acrylamide and diallyldimethylammonium salt; CTFA name: Polyquaternarium-7), "LUBIQUAT FC370" (available from BASF; copolymer of 1-vinyl-2-pyrrolidone and 1-vinyl-3-methyl imidazolium salt; CTFA name: Polyquaternarium-16), "GAFQUAT 755N" (available from ISP; copolymer of 1-vinyl-2-pyrrolidone and dimethylaminoethyl methacrylate; CTFA name: Polyquaternarium-11), "Ucare Polymer JR Series" and "Ucare Polymer LR Series" (available from Amerchol Corp.; salt of reaction product of trimethyl ammonium-substituted epoxide and hydroxyethyl cellulose; CTFA name: Polyquaternarium-10), "Poise C-60H", "Poise C-80M" and "Poise C-150L" (all available from Kao Corp.; salt of reaction product of trimethyl ammonium-substituted epoxide and hydroxyethyl cellulose; CTFA name: Polyquaternarium-10) and "JAGUAR Series" (available from Rhodia Inc.; guar hydroxypropyl triammonium chloride).

These water-soluble cationic polymers may be used alone or in combination of any two or more thereof. The content of the water-soluble cationic polymer in the water-based shampoo of the present invention is preferably from 0.01 to 5% by mass, and more preferably from 0.05 to 2% by mass and still more preferably from 0.1 to 1% by mass in view of smoothness upon from shampooing to rinsing.

In addition, the water-based shampoo of the present invention may also contain a pearling agent containing an ethylene glycol monoalkyl ester or an ethylene glycol dialkyl ester. Examples of the ethylene glycol monoalkyl ester include an ethylene glycol monostearyl ester and an ethylene glycol monobehenyl ester. Examples of the ethylene glycol dialkyl ester include an ethylene glycol distearyl ester and an ethylene glycol dibehenyl ester. Further, as the pearling agent, there may also be used ethylene glycol monoalkyl ethers such as ethylene glycol monostearyl ether, and ethylene glycol dialkyl ethers such as ethylene glycol distearyl ether. These pearling agents may be used in combination of any two or more thereof. The content of the pearling agent in the water-based shampoo of the present invention is preferably from 0.1 to 10% by mass, more preferably from 0.5 to 5% by mass and still more preferably 1 to 4% by mass in order to improve a stability of the shampoo and a smoothness upon foaming and rinsing.

The water-based shampoo of the present invention may further contain a cationic surfactant, silicones other than those contained in the above silicone blend forming the oil droplets, etc.

Examples of the cationic surfactant suitably used in the present invention include the following compounds (i) to (vi).

(i) Alkyltrimethylammonium Salt

Examples of the alkyltrimethylammonium salt include compounds represented by the following general formula:

$$R^{11}-N^+(Me)_3 X^-$$

wherein $R^{11}$ is an alkyl group having 12 to 22 carbon atoms; Me is methyl; and $X^-$ is a halogen ion such as chlorine ion and bromine ion.

(ii) Alkoxytrimethylammonium Salt

Examples of the alkoxytrimethylammonium salt include compounds represented by the following general formula:

$$R^{12}\text{—}O\text{—}R^{13}\text{—}N^+(Me)_3 X^-$$

wherein $R^{12}$ is an alkyl group having 12 to 22 carbon atoms; $R^{13}$ is an ethylene group or a propylene group; Me is methyl; and $X^-$ is the same as defined above.

(iii) Dialkyldimethylammonium Salt

Examples of the dialkyldimethylammonium salt include compounds represented by the following general formula:

$$R^{14}{}_2\text{—}N^+(Me)_2 X^-$$

wherein $R^{14}$ is an alkyl group having 12 to 22 carbon atoms or a benzyl group; Me is methyl; and X is the same as defined above.

(iv) Alkyldimethylamine and Salt Thereof.

Examples of the alkyldimethylamine and salt thereof include compounds represented by the following general formula:

$$R^{15}\text{—}N(Me)_2$$

wherein $R^{15}$ is an alkyl group having 12 to 22 carbon atoms; and Me is methyl.

(v) Alkoxydimethylamine and Salt Thereof.

Examples of the alkoxydimethylamine and salt thereof include compounds represented by the following general formula:

$$R^{16}\text{—}O\text{—}R^{17}\text{—}N(Me)_2$$

wherein $R^{16}$ is an alkyl group having 12 to 22 carbon atoms; $R^{17}$ is an ethylene group or a propylene group; and Me is methyl.

(vi) Alkylamidodimethylamine and Salt Thereof.

Examples of the alkylamidodimethylamine and salt thereof include compounds represented by the following general formula:

$$R^{18}\text{—}C(\!=\!O)NH\text{—}R^{19}\text{—}N(Me)_2$$

wherein $R^{18}$ is an alkyl group having 11 to 21 carbon atoms; $R^{19}$ is an ethylene group or a propylene group; and Me is methyl.

Examples of the cationic surfactant other than the above compounds (i) to (vi) include lanolin fatty acid aminopropylethyldimethylammonium ethylsulfates (ethylsulfates of alkanoyl aminopropyl dimethyl ethylammonium; the alkanoyl group is derived from lanolin), lanolin fatty acid aminoethyltriethylammonium ethylsulfates, lanolin fatty acid aminopropyltriethylammonium ethylsulfates, lanolin fatty acid aminoethyltrimethylammonium methylsulfates, lanolin fatty acid aminopropylethyldimethylammonium methylsulfates, isoalkanoic acid ($C_{14}$ to $C_{20}$) aminopropylethyldimethylammonium ethylsulfates, isoalkanoic acid ($C_{18}$ to $C_{22}$) aminopropylethyldimethylammonium ethylsulfates, isostearic acid aminopropylethyldimethylammonium ethylsulfates, isononanoic acid aminopropylethyldimethylammonium ethylsulfates and alkyltrimethylammonium saccharin.

These cationic surfactants may be used in combination of any two or more thereof. The content of the cationic surfactant in the water-based shampoo of the present invention is preferably 0.01 to 10% by mass, more preferably 0.05 to 6% by mass, still more preferably 0.3 to 3% by mass and further still more preferably 0.5 to 2% by mass in view of good smoothness upon from shampooing to rinsing.

Examples of the silicones other than those used in the silicone blend include the following compounds.

(a) Polydimethylsiloxane Represented by the Following General Formula:

$$R(CH_3)_2SiO\text{—}[(CH_3)_2SiO]_m\text{—}Si(CH_3)_2R$$

wherein R is methyl or hydroxyl; and m is a number of 1 to 20,000.

(b) Amino-Modified Silicone

Amino-modified silicones other than those used as the component (B) may also be used in the present invention. In particular, such amino-modified silicones having an average molecular weight of about 3,000 to 100,000 which are described under the name "Amodimethicone" in the CTFA dictionary (Cosmetic Ingredient Dictionary; US), the 3rd edition, are preferred. Examples of commercially available product of the amino-modified silicones include "SM 8704C" available from Toray Dow Corning Silicone Co., Ltd., "DC 929" available from Dow Corning Corp., "KT 1989" available from GE Toshiba Silicone Co., Ltd., and "8500 Conditioning Agent" available from Toray Dow Corning Silicone Co., Ltd.

(c) Other Silicones

Examples of silicones other than the above silicones include polyether-modified silicones, methylphenyl polysiloxanes, fatty acid-modified silicones, alcohol-modified silicones, alkoxy-modified silicones, epoxy-modified silicones, fluorine-modified silicones, cyclic silicones and alkyl-modified silicones.

These silicones may be used in combination of any two or more thereof. The content of the silicones in the water-based shampoo of the present invention is preferably 0.01 to 10% by mass, more preferably 0.05 to 6% by mass, still more preferably 0.3 to 3% by mass and further still more preferably 0.5 to 2% by mass in view of good smoothness upon from shampooing to rinsing.

In addition, as the other conditioning agent, there may also be used oil agents. Examples of the oil agents include hydrocarbons such as squalene, squarane, liquid paraffins, liquid isoparaffins and cycloparaffins; glycerides such as castor oil, cacao oil, mink oil, avocado oil and olive oil; waxes such as beeswax, spermaceti wax, lanolin and carnauba wax; alcohols such as cetyl alcohol, oleyl alcohol, stearyl alcohol, isostearyl alcohol, 2-octyl dodecanol and glycerin; esters such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanoate and tridecyl isononanoate; higher fatty acids such as capric acid, lauric acid, myristic acid, palmitic acid, stearic acid, behenic acid, oleic acid, coconut oil fatty acid, isostearic acid and isopalmitic acid; and others such as isostearyl glyceryl ether and polyoxypropylene butyl ether. Among these oil agents, preferred are higher alcohols, and more preferred are myristyl alcohol, cetyl alcohol and stearyl alcohol. These oil agents may be used alone or in combination of any two or more thereof. The content of the oil agents in the water-based shampoo of the present invention is preferably 0.2 to 2% by mass, more preferably 0.3 to 1.8% by mass and still more preferably 0.5 to 1.5% by mass.

The water-based shampoo of the present invention may also contain a viscosity modifier. Examples of the viscosity modifier include hydroxyethyl cellulose, methyl cellulose, polyethylene glycol, polypropylene glycol, ethylene glycol, propylene glycol, isoprene glycol, ethanol, benzyl alcohol, benzyl oxyethanol, phenoxyethanol, clay minerals, and salts such as sodium chloride, ammonium chloride and sodium citrate. Among these viscosity modifiers, preferred are benzyl alcohol, ethanol, polypropylene glycol, sodium chloride and sodium citrate. These viscosity modifiers may be used in combination of any two or more thereof. The content of the viscosity modifier used in the water-based shampoo of the present invention is preferably 0.01 to 5% by mass, more preferably 0.05 to 4% by mass and still more preferably 0.1 to 3% by mass in view of sufficient amount and quality of foam produced.

The water-based shampoo of the present invention may also contain, in addition to the above components, other components ordinarily used in conventional shampoos according to objects and applications. Examples of the other components include antidandruff agents; vitamins; antibacterial agents; anti-inflammatory agents; antiseptic agents; chelating agents; humectants such as sorbitol and pantenol; colorants such as dyes and pigments; extracts such as polar solvent extracts of eucalyptus, proteins obtained from shells having a pearl layer or pearls or hydrolyzed products thereof, proteins obtained from silk or hydrolyzed products thereof, protein-containing extracts obtained from seeds of leguminous plants, ginseng extracts, rice embryo extracts, *fucus* extracts, aloe extracts, *alpinia* leaf extracts and *chlorella* extracts; pearling agents such as titanium oxide; perfumes; pigments; ultraviolet light absorbers; antioxidants; and components described in "ENCYCLOPEDIA OF SHAMPOO INGREDIENTS (MICELLE PRESS)".

The pH of the water-based shampoo of the present invention when applied to hair is preferably controlled to 2 to 6, more preferably 3 to 5 and still more preferably 3.5 to 4.5 as measured at 25° C. with respect to a solution obtained by diluting the shampoo with water 20 times by weight, in view of improving luster and manageability of the hair. Examples of the pH modifier suitably used for the above purpose include organic acids, in particular, α-hydroxy acids. Specific examples of the organic acids include malic acid, citric acid, lactic acid and glycolic acid. These organic acids may be used in combination of any two or more thereof. The amount of the organic acid used in the water-based shampoo of the present invention is preferably 0.01 to 5% by mass, more preferably 0.1 to 3% by mass and still more preferably 0.3 to 2% by mass in view of improving a quality of foam and a softness of hair upon shampooing. Further, the other pH modifier, e.g., bases such as sodium hydroxide, potassium hydroxide and ammonium chloride may be used in combination with the organic acid.

The configuration of the water-based shampoo of the present invention may be appropriately selected from liquid, gel, etc. In particular, the water-based shampoo is preferably used in the form of a liquid by using water or a lower alcohol, especially water, as a solvent.

EXAMPLES

Evaluation Methods
(1) Foamability

Figure 1:
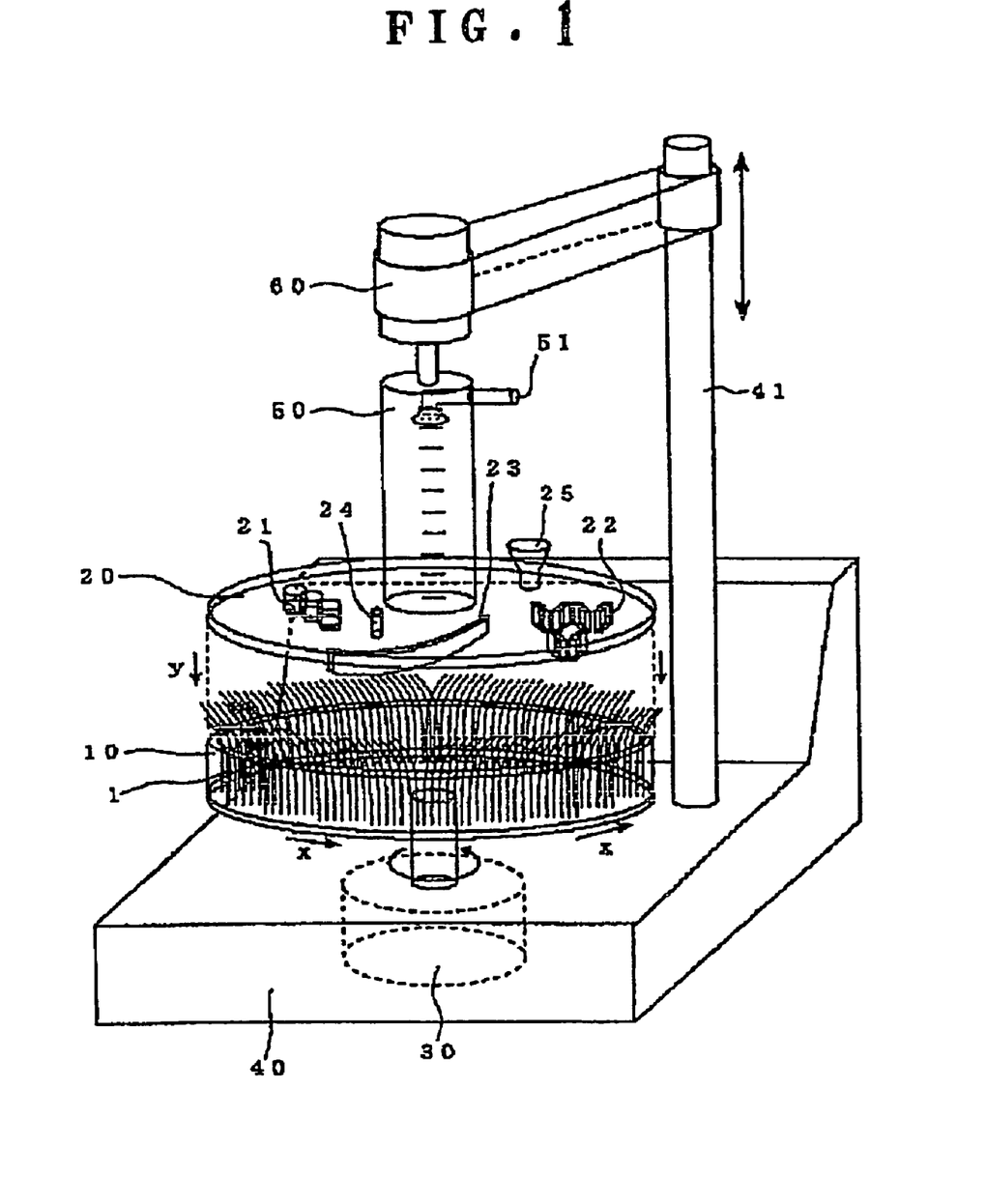
FIG. 1 is a schematic view of an apparatus used for evaluation of a shampoo.

Using an apparatus shown in FIG. 1 (as described in JP 10-73584A) and the following procedure, hair with 0.3 mL of a model sebum was treated with 1.5 mL of a sample to be evaluated to measure an amount of foam produced. The foamability was evaluated by the time required until the amount of foam produced reached 25 mL.

Figure 2:
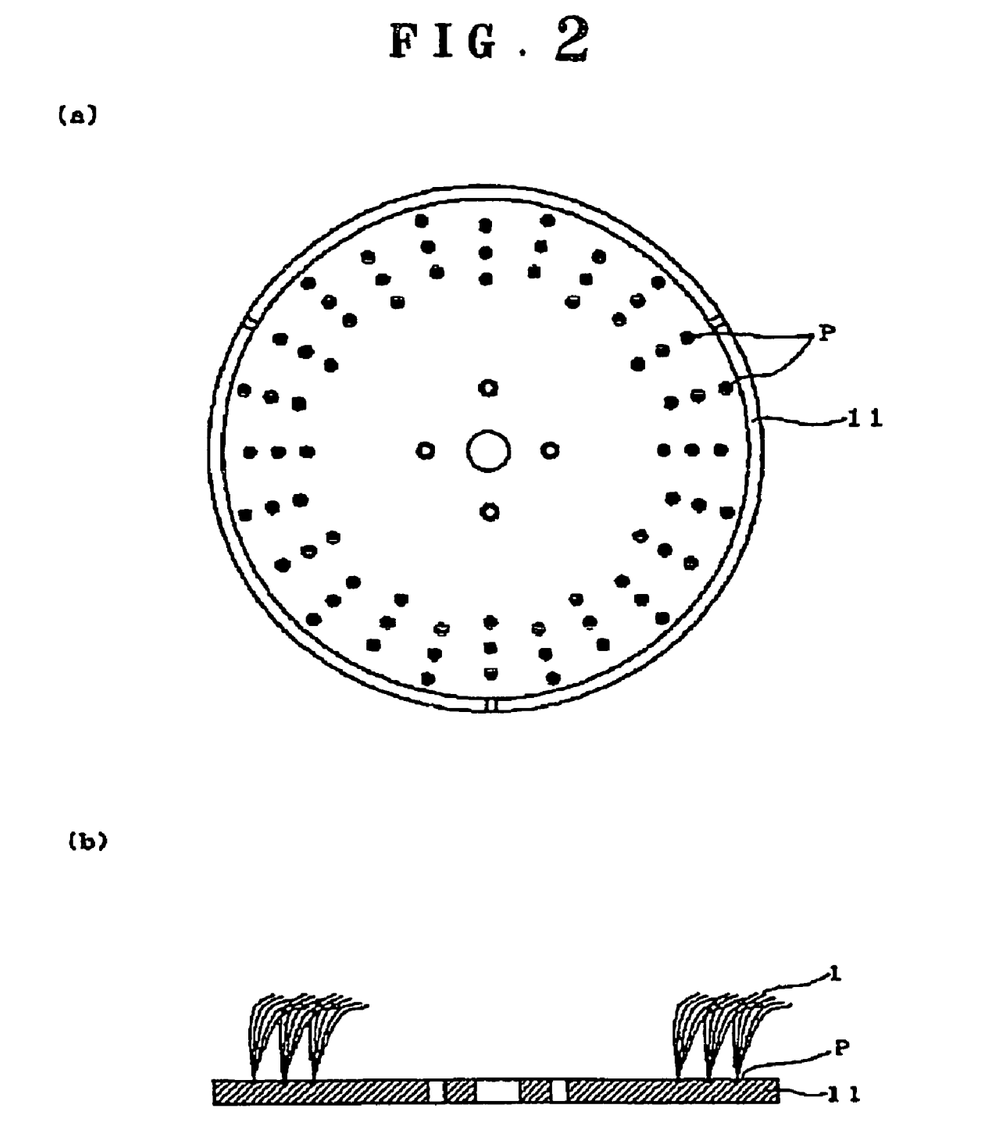
FIG. 2(a) is a plan view showing a disk before planting a hair thereon.
FIG. 2(b) is a sectional view showing the disk with a hair planted thereon.

More specifically, in the apparatus shown in FIGS. 1 and 2, there was used a test hair 1 obtained by planting 30 g of hair having a length of 90 mm on a disk 11 having a diameter of about 160 mm. Further, there were used a container 10 of a cylindrical shape having a diameter of 160 mm and a height of 220 mm, and a lid 20 formed with three cylindrical protrusions as first protrusions 21 each having a diameter of 15 mm and a height of 12 mm and nine protrusions as second protrusions 22 each having a length of 10 mm, a width of 2 mm and a height of 12 mm. The rotating speed of the container 10 was set to 70 rpm using a motor.

In the method for evaluation of foamability using the above apparatus, first, the test hair was wetted with 30 g of water, and the model sebum was added thereto. Thereafter, the sample to be evaluated was applied to the test hair, and then the test hair 1 and the protrusions 21 and 22 were brought into a relative sliding contact with each other to collect a foam produced into a metering device 50. In this method, the amount of foam collected was recorded every 50 s from immediately after initiation of the sliding motion. The evaluation criteria are as follows.

<Evaluation Criteria>
 A: Less than 100 s
 B: Not less than 100 s but less than 200 s
 C: Not less than 200 s but less than 300 s
 D: Not less than 300 s (2) Smoothness Upon Rinsing A human hair bundle having a length 25 cm, a width of 5.5 cm and a weight of 10 g was lightly rinsed with hot water at 40° C. After removing an excess amount of water from the hair bundle, 0.5 g of the shampoo was applied thereto and fully foamed for about 30 s. Thereafter, the foamed hair bundle was rinsed with 40° C. hot water poured at a flow rate of 2 L/min to conduct a sensory evaluation for smoothness. The sensory evaluation for the smoothness was performed by 5 persons, and the smoothness was evaluated by a sum of the five values given by the 5 persons. The evaluation criteria are as follows.
 4: Good smoothness
 3: Some smoothness
 2: Poor smoothness
 1: No smoothness (3) Luster and Manageability after Drying The hair bundle treated in the same manner as in the above evaluation for smoothness was rinsed with a flowing water at 40° C. (flow rate: 2 L/min), wiped with towel to fully remove water therefrom, and then naturally dried. After drying, the hair bundle was observed by naked eyes to evaluate luster and manageability thereof. The evaluation for luster and manageability of the hair bundle was performed by 5 persons, and the luster and manageability of the hair bundle were evaluated by a sum of the five values given by the 5 persons. The evaluation criteria are as follows.
 4: Good
 3: Good to some extent
 2: Not good
 1: Poor (4) Smoothness after Drying The hair bundle treated in the same manner as in the above evaluation for smoothness was rinsed with a flowing water at 40° C. (flow rate: 2 L/min), wiped with towel to fully remove water therefrom, and then naturally dried. After drying, the hair bundle was evaluated for smoothness. The evaluation for the smoothness after drying was performed by 5 persons, and the smoothness after drying was evaluated by a sum of the five values given by the 5 persons. The evaluation criteria are as follows.
 4: Good smoothness
 3: Some smoothness
 2: Poor smoothness
 1: No smoothness Production Example 1

Production of Silicone Blend Emulsion (Silicone Blend 1 of the Present Invention) [Component (A): Polydimethylsiloxane Having a Viscosity of 1,000 mm²/s; Component (B): "Silicone SS-3588" Available from Toray Dow Corning Silicone Co., Ltd.; Ratio of Component (A) to Component (B)=90:10]

Using a "Three-One Motor BL600" available from Heidon Corp., 54% by mass of polydimethylsiloxane having a viscosity of 1,000 mm²/s and 6% by mass of "Silicone SS-3588" were mixed together at a rotating speed of 200 rpm until obtaining a uniform mixture. Next, while stirring the obtained mixture at a rotating speed of 200 rpm, 4.5% by mass of polyoxyethylene (23) lauryl ether and 1.5% by mass of polyoxyethylene (4) lauryl ether were added thereto, and the resultant mixture was mixed for 10 min. Thereafter, while stirring the mixture at a rotating speed of 200 rpm, 25% by mass of water was added thereto, and the obtained mixture was successively stirred for 5 min at a rotating speed of 5,000 rpm using "AGI-HOMOMIXER" (f2/5 Model; No. 023010) available from Tokushu Kika Kogyo Co., Ltd. Next, the resultant mixture was mixed with 9% by mass of water, and further stirred for 5 min at a rotating speed of 5,000 rpm using "AGI-HOMOMIXER" (f2/5 Model; No. 023010) available from Tokushu Kika Kogyo Co., Ltd.

The average particle size of emulsified particles contained in the silicone emulsion having an adequate concentration was measured by laser diffraction using "LS-130" available from Coulter Inc. As a result, it was confirmed that the average particle size was 0.7 μm.

Production Example 2

Production of Silicone Blend Emulsion (Silicone Blend 2 of the Present Invention) [Component (A): Polydimethylsiloxane Having a Viscosity of 10,000 mm²/s; Component (B): "Silicone SS-3588" Available from Toray Dow Corning Silicone Co., Ltd.; Ratio of Component (A) to Component (B) 90:10]

The same procedure as in Production Example 1 was repeated except that the polydimethylsiloxane was replaced with polydimethylsiloxane having a viscosity of 10,000 mm²/s, thereby producing a silicone blend emulsion.

The average particle size of emulsified particles contained in the obtained silicone emulsion was measured by the same method as in Production Example 1. As a result, it was confirmed that the average particle size was 0.7 μm.

Production Example 3

Production of Silicone Blend Emulsion (Silicone Blend 3 of the Present Invention) [Component (A): Mixture Containing Polydimethylsiloxane Having a Viscosity of 10,000 mm²/s and Polydimethylsiloxane Having a Viscosity of 10 mm²/s at a Mixing Ratio of 90:10; Component (B): "Silicone SS-3588" Available from Toray Dow Corning Silicone Co., Ltd.; Ratio of Component (A) to Component (B)=90:10; Viscosity of Mixture: 5,000 mm²/s]

The same procedure as in Production Example 1 was repeated except that the polydimethylsiloxane was replaced with 48.6% by mass of polydimethylsiloxane having a viscosity of 10,000 mm²/s and 5.4% by mass of polydimethylsiloxane having a viscosity of 10 mm²/s, and the rotating speed of the "AGI-HOMOMIXER" was changed to 1,500 rpm, thereby producing a silicone blend emulsion.

The average particle size of emulsified particles contained in the obtained silicone emulsion was measured by the same method as in Production Example 1. As a result, it was confirmed that the average particle size was 8.5 μm.

Production Example 4

Production of Silicone Blend Emulsion (Silicone Blend 4 of the Present Invention) [Component (A): Polydimethylsiloxane Having a Viscosity of 100,000 mm²/s; Component (B): "Silicone SS-3588" Available from Toray Dow Corning Silicone Co., Ltd.; Ratio of Component (A) to Component (B)=90:10]

The same procedure as in Production Example 1 was repeated except that the polydimethylsiloxane was replaced with polydimethylsiloxane having a viscosity of 100,000 mm²/s, thereby producing a silicone blend emulsion.

The average particle size of emulsified particles contained in the obtained silicone emulsion was measured by the same method as in Production Example 1. As a result, it was confirmed that the average particle size was 0.7 μm.

Production Example 5

Production of Silicone Blend Emulsion (Silicone Blend 5 of the Present Invention) [Component (A): Mixture Containing Polydimethylsiloxane Having a Viscosity of 1,000,000 mm²/s and Decamethylcyclopentasiloxane at a Mixing Ratio of 70:30; Component (B): "Silicone SS-3588" Available from Toray Dow Corning Silicone Co., Ltd.; Ratio of Component (A) to Component (B)=90:10; Viscosity of Mixture: 25,000 mm²/s]

The same procedure as in Production Example 1 was repeated except that the polydimethylsiloxane was replaced with a mixture containing polydimethylsiloxane having a viscosity of 1,000,000 mm²/s and decamethylcyclopentasiloxane at a mixing ratio of 70:30, thereby producing a silicone blend emulsion.

The average particle size of emulsified particles contained in the obtained silicone emulsion was measured by the same method as in Production Example 1. As a result, it was confirmed that the average particle size was 0.7 μm.

Production Example 6

Production of Silicone Blend Emulsion (Silicone Blend 6 of the Present Invention) [Component (A): Mixture Containing Polydimethylsiloxane Having a Viscosity of 6,000,000 mm²/s and Polydimethylsiloxane Having a Viscosity of 500 mm²% s at a Mixing Ratio of 70:30; Component (B): "Silicone SS-3588" Available from Toray Dow Corning Silicone Co., Ltd.; Ratio of Component (A) to Component (B)=30:70; Viscosity of Mixture: 9,000 mm²/s]

The same procedure as in Production Example 1 was repeated except that the polydimethylsiloxane was replaced with a mixture containing polydimethylsiloxane having a viscosity of 6,000,000 mm²/s and polydimethylsiloxane having a viscosity of 500 mm²/s at a mixing ratio of 30:70, thereby producing a silicone blend emulsion.

The average particle size of emulsified particles contained in the obtained silicone emulsion was measured by the same method as in Production Example 1. As a result, it was confirmed that the average particle size was 0.6 μm.

Production Example 7

Production of Silicone Blend Emulsion (Silicone Blend 7 of the Present Invention) [Component (A): Polydimethylsiloxane Having a Viscosity of 10,000 mm²/s; Component (B): "Silicone SS-3588" Available from Toray Dow Corning Silicone Co., Ltd.; Ratio of Component (A) to Component (B)=95:5]

Using a "Three-One Motor BL600" available from Heidon Corp., 54% by mass of polydimethylsiloxane having a viscosity of 10,000 mm$^2$/s and 6% by mass of "Silicone SS-3588" were mixed together at a rotating speed of 200 rpm until obtaining a uniform mixture. Next, while stirring the obtained mixture at a rotating speed of 200 rpm, 7% by mass of cetyltrimethylammonium chloride was added thereto, and the resultant mixture was mixed for 10 min. Thereafter, while stirring the mixture at a rotating speed of 200 rpm, 25% by mass of water was added thereto, and the obtained mixture was successively stirred for 5 min at a rotating speed of 2,000 rpm using "AGI-HOMOMIXER" (f2/5 Model; No. 023010) available from Tokushu Kika Kogyo Co., Ltd. Next, the resultant mixture was mixed with 8% by mass of water, and further stirred for 5 min at a rotating speed of 2,000 rpm using "AGI-HOMOMIXER" (f2/5 Model; No. 023010) available from Tokushu Kika Kogyo Co., Ltd.

The average particle size of emulsified particles contained in the silicone emulsion having an adequate concentration was measured by laser diffraction using "LS-130" available from Coulter Inc. As a result, it was confirmed that the average particle size was 80 μm.

Production Example 8

Production of Silicone Blend Emulsion (Comparative Silicone Blend 1) [Emulsion of a Silicone Blend Composed of Polydimethylsiloxane Having a Viscosity of 1,000,000 mm$^2$/s and Amino-Modified Silicone "Q2-8220" Available from Dow Corning Corp.; Ratio of Polydimethylsiloxane to Amino-Modified Silicone=75:25]

The silicone blend having the above composition was produced by the method described in Example 1 of JP 2004-526806A.

Examples 1 to 7 and Comparative Examples 1 to 3

The shampoos shown in Table 1 were prepared and evaluated according to the above evaluation methods. Meanwhile, the pH values shown in Table 1 were measured at 25° C. with respect to a solution obtained by diluting the respective shampoos with water 20 times by weight.

TABLE 1-1

| Components | Examples | | | | | | | Comparative Examples | | |
|---|---|---|---|---|---|---|---|---|---|---|
| | 1 | 2 | 3 | 4 | 5 | 6 | 7 | 1 | 2 | 3 |
| Silicone blend 1 | 2 | — | — | — | — | — | — | — | — | — |
| Silicone blend 2 | — | 2 | — | — | — | — | — | — | — | — |
| Silicone blend 3 | — | — | 2 | — | — | — | — | — | — | — |
| Silicone blend 4 | — | — | — | 2 | — | — | — | — | — | — |
| Silicone blend 5 | — | — | — | — | 2 | — | — | — | — | — |
| Silicone blend 6 | — | — | — | — | — | 2 | — | — | — | — |
| Silicone blend 7 | — | — | — | — | — | — | 2 | — | — | — |
| Comparative silicone blend 1 | — | — | — | — | — | — | — | 2 | — | — |
| Amino-modified silicone *[1] | — | — | — | — | — | — | — | — | 0.25 | — |
| Block copolymer *[2] | — | — | — | — | — | — | — | — | — | 0.1 |
| Dimethyl polysioxane *[3] | — | — | — | — | — | — | — | — | 0.75 | 1.1 |
| Lauryl ether (1) ammonium sulfate *[4] | 12 | 12 | 12 | 12 | 12 | 12 | 12 | 12 | 12 | 12 |
| Isodecyl glyceryl ether | 0.5 | 0.5 | 0.5 | 0.5 | 0.5 | 0.5 | 0.5 | 0.5 | 0.5 | 0.5 |
| Lauryl amidopropylbetaine | 1.5 | 1.5 | 1.5 | 1.5 | 1.5 | 1.5 | 1.5 | 1.5 | 1.5 | 1.5 |
| Myristyl alcohol | 1 | 1 | 1 | 1 | 1 | 1 | 1 | 1 | 1 | 1 |
| Cocoylmonoethanolamine | 0.5 | 0.5 | 0.5 | 0.5 | 0.5 | 0.5 | 0.5 | 0.5 | 0.5 | 0.5 |
| Ethylene glycol distearyl ester | 2 | 2 | 2 | 2 | 2 | 2 | 2 | 2 | 2 | 2 |
| Cationized hydroxyethyl cellulose *[5] | 0.5 | 0.5 | 0.5 | 0.5 | 0.5 | 0.5 | 0.5 | 0.5 | 0.5 | 0.5 |
| Benzyl alcohol | 0.5 | 0.5 | 0.5 | 0.5 | 0.5 | 0.5 | 0.5 | 0.5 | 0.5 | 0.5 |
| Sodium chloride | 0.2 | 0.2 | 0.2 | 0.2 | 0.2 | 0.2 | 0.2 | 0.2 | 0.2 | 0.2 |
| Malic acid | 0.6 | 0.6 | 0.6 | 0.6 | 0.6 | 0.6 | 0.6 | 0.6 | 0.6 | 0.6 |
| Purified water | balance | balance | balance | balance | balance | balance | balance | balance | balance | balance |
| Total | 100 | 100 | 100 | 100 | 100 | 100 | 100 | 100 | 100 | 100 |
| Evaluation | | | | | | | | | | |
| pH | 3.7 | 3.7 | 3.7 | 3.7 | 3.7 | 3.7 | 3.7 | 3.7 | 3.7 | 3.7 |
| Foamability | A | A | A | A | A | A | A | B | C | A |
| Smoothness upon rinsing | 17 | 19 | 20 | 19 | 17 | 15 | 17 | 9 | 7 | 8 |
| Luster and manageability after drying | 16 | 19 | 20 | 19 | 19 | 18 | 17 | 14 | 14 | 15 |
| Smoothness after drying | 19 | 20 | 20 | 19 | 18 | 17 | 15 | 12 | 10 | 11 |

Note:
*[1]Amino-modified silicone "Q2-8220" available from Dow Corning Corp.;
*[2]Block copolymer "Silicone SS-3588" available from Toray Dow Corning Silicone Co., Ltd.;
*[3]Polydimethylsiloxane having a viscosity of 100,000 mm$^2$/s;
*[4]Lauryl ether (1) ammonium sulfate; weight-average molar number of addition of ethyleneoxide: 1;
*[5]Cationized hydroxyethyl cellulose "Polymer JR-400" available from Amerchol Corp.

In the following Examples 8 to 12, the conditioning shampoos having the following compositions were prepared and evaluated with respect to foamability, smoothness upon foaming and rinsing, luster and manageability of finished hair, etc.

Example 8

| Composition of Conditioning Shampoo | |
|---|---|
| (Components) | (mass %) |
| Lauryl ether (1) ammonium sulfate (average molar number of addition of ethyleneoxide: 1) | 14.0 |
| Silicone blend 3 | 1.7 |
| Cationized hydroxyethyl cellulose "Poise C-80M" available from Kao Corp. | 0.3 |
| Cationized guar gum "Jaguar C-13S" available from Rhodia Inc. | 0.3 |
| Dimethyldiallylammonium/acrylamide copolymer "MERQUAT 550" available from NALCO Co. | 1.2 |
| Ethylene glycol distearyl ester | 2.0 |
| Isodecyl glyceryl ether | 0.5 |
| Lauryl amidopropylbetaine | 1.0 |
| Myristyl alcohol | 0.5 |
| Cocoyl monoethanolamide | 0.8 |
| Polyoxyethylene (16) lauryl ether | 0.7 |
| Amino-modified silicone "8500 Conditioning Agent" available from Toray Dow Corning Silicone Co., Ltd. | 0.3 |
| Polypropylene glycol (Mw = 400) | 0.5 |
| Benzyl alcohol | 0.3 |
| Ethanol | 3.0 |
| Pantenol | 0.05 |
| Silk extract | 0.05 |
| Sodium chloride | 0.5 |
| Perfume | q.s. |
| Malic acid | 0.5 |
| Lactic acid | Amount capable of adjusting the pH to 3.9 |
| Ion-exchanged water | Balance |

Example 9

| Composition of Conditioning Shampoo | |
|---|---|
| (Components) | mass % |
| Lauryl ether (2) ammonium sulfate (average molar number of addition of ethyleneoxide: 2) | 13.0 |
| Silicone blend 2 | 3.5 |
| Cationized hydroxyethyl cellulose "Polymer JR-400" available from Amerchol Corp. | 0.5 |
| Diallyl quaternary ammonium salt/acrylamide copolymer "MARCOAT 550" available from NALCO Co. | 2.4 |
| Ethylene glycol distearyl ester | 3.0 |
| Isodecyl glyceryl ether | 0.7 |
| Lauryl amidopropylbetaine | 2.0 |
| Cocoyl monoethanolamide | 0.5 |
| Myristyl alcohol | 1.0 |
| Cetyl alcohol | 0.5 |
| Polyoxyethylene (16) lauryl ether | 2.0 |
| Highly-polymerized polymethylsiloxane emulsion ("Silicone CF2450" particle size: 0.2 to 0.8 μm; available from Toray Dow Corning Silicone Co., Ltd.) | 0.5 |
| Benzyl alcohol | 1.0 |
| Polypropylene glycol (Mw = 400) | 0.2 |
| Sodium chloride | 1.0 |
| Hydrolyzed conchiolin solution (dry solid content: 3% by mass) | 0.05 |
| Ginseng extract (dry solid content: 3% by mass) | 0.05 |
| Soybean extract (dry solid content: 0.4% by mass) | 0.05 |
| Eucalyptus extract (dry solid content: 0.2% by mass) | 0.05 |
| Rice embryo oil | 0.05 |
| Glycolic acid | 1.0 |
| Perfume | q.s. |
| Sodium hydroxide | Amount capable of adjusting the pH to 3.9 |
| Ion-exchanged water | Balance |

Example 10

| Composition of Conditioning Shampoo | |
|---|---|
| (Components) | (mass %) |
| Lauryl ether (1) sodium sulfate (average molar number of addition of ethyleneoxide: 1) | 16.0 |
| Silicone blend 2 | 1.2 |
| Cationized hydroxyethyl cellulose "Polymer JR-30M" available from Amerchol Corp. | 0.5 |
| Ethylene glycol distearyl ester | 3.0 |
| Cocoyl monoethanolamide | 0.8 |
| Stearyl alcohol | 0.8 |
| Highly-polymerized polymethylsiloxane emulsion ("Silicone CF2450"; particle size: 20 to 80 μm; available from Toray Dow Corning Silicone Co., Ltd.) | 1.6 |
| Glycerin | 0.5 |
| Sodium chloride | 0.2 |
| Benzyloxyethanol | 0.5 |
| Malic acid | 0.7 |
| Perfume | q.s. |
| Lactic acid | 0.1 |
| Citric acid | Amount capable of adjusting the pH to 5.5 |
| Ion-exchanged water | Balance |

Example 11

| Composition of Conditioning Shampoo | |
|---|---|
| (Components) | (mass %) |
| Lauryl ether (2.5) sodium sulfate (average molar number of addition of ethyleneoxide: 2.5) | 15.0 |
| Silicone blend 1 | 1.7 |
| Cationized guar gum "Jaguar C-14S" available from Rhodia Inc. | 0.5 |
| Ethylene glycol distearyl ester | 2.0 |
| Lauryl amidopropylbetaine | 3.0 |
| Cocoyl monoethanolamide | 0.8 |
| Polyoxyethylene (16) lauryl ether | 2.0 |
| Stearoxypropyldimethylamine malate | 0.5 |
| Polypropylene glycol (Mw = 400) | 0.5 |
| Sodium chloride | 1.0 |
| Malic acid | 0.8 |

-continued

| Composition of Conditioning Shampoo | |
|---|---|
| (Components) | (mass %) |
| Citric acid | 0.75 |
| Sodium hydroxide | Amount capable of adjusting the pH to 3.5 |
| Ion-exchanged water | Balance |

Example 12

| Composition of Conditioning Shampoo | |
|---|---|
| (Components) | (mass %) |
| Lauryl ether (1) ammonium sulfate (average molar number of addition of ethyleneoxide: 1) | 14.0 |
| Silicone blend 7 | 1.5 |
| Cationized hydroxyethyl cellulose "Polymer JR-400" available from Amerchol Corp. | 0.4 |
| Ethylene glycol distearyl ester | 2.0 |
| Isodecyl glyceryl ether | 1.5 |
| Cocoyl amidopropylbetaine | 1.0 |
| Lauryl hydroxysulfobetaine | 1.0 |
| Lauric acid | 0.5 |
| Oleic acid | 0.7 |
| Cocoyl benzalkonium chloride | 0.5 |
| Ethanol | 0.5 |
| Fucus extract | 0.05 |
| Malic acid | 0.7 |
| Perfume | q.s. |
| Sodium hydroxide | Amount capable of adjusting the pH to 5.5 |
| Ion-exchanged water | Balance |

The shampoos obtained in Examples 8 to 12 exhibited rapid foaming and good smoothness upon foaming and rinsing as well as good luster and manageability of finished hair, and were excellent in stability.

INDUSTRIAL APPLICABILITY

The water-based shampoo of the present invention exhibits a smooth feel of hair upon shampooing and rinsing, and imparts good luster and manageability to finished hair.

What is claimed is:

1. A water-based shampoo comprising silicone oil droplets dispersed therein, said oil droplets comprising (A) 70 to 97% by mass of polydimethylsiloxane and (B) 3 to 30% by mass of a copolymer having a block chain constituted of an amino-modified organopolysiloxane chain and a polyoxyalkylene chain, wherein the content of said oil droplets in said shampoo is 0.5 to 2% by mass prepared by dispersing a pre-mix of (A) and (B).

2. The water-based shampoo according to claim 1, wherein the component (B) is a copolymer represented by the general formula (1):

wherein $R^1$ is a hydrogen atom or a monovalent hydrocarbon group having 1 to 6 carbon atoms; $R^2$ is $R^1$ or E; E is a group represented by $-R^3-Z$ wherein $R^3$ is a direct bond or a divalent hydrocarbon group having 1 to 20 carbon atoms, and Z is a primary, secondary or tertiary amino-containing group or an ammonium-containing group; Y is a divalent group; a is a number of 2 or more; b is a number of 1 or more; n is a number of 2 to 10; c is a number of 4 or more; d is a number of 2 or more; and a plurality of the $R^1$ groups, a plurality of the $R^2$ groups and a plurality of the E groups are respectively the same or different.

3. The water-based shampoo according to claim 1, wherein the component (A) has a viscosity of 100,000 mm²/s or lower as measured at 25° C.

4. The water-based shampoo according to claim 1, wherein the silicone oil droplets each have a particle size of 100 μm or less.

5. The water-based shampoo according to claim 1, further comprising an anionic surfactant in an amount of 1 to 30% by mass.

6. The water-based shampoo according to claim 1, wherein the oil droplets comprise 85 to 95% by mass of the polydimethylsiloxane.

7. The water-based shampoo according to claim 1, wherein said shampoo has a pH of 2 to 6 as measured at 25° C. with respect to a solution obtained by diluting the shampoo with water 20 times by weight.

* * * * *